United States Patent
Green et al.

(10) Patent No.: US 7,169,159 B2
(45) Date of Patent: *Jan. 30, 2007

(54) SAFETY TROCAR

(75) Inventors: David T. Green, Westport, CT (US); David A. Nicholas, Trumbull, CT (US); Daniel Shichman, Trumbull, CT (US)

(73) Assignee: United States Surgical Corporation, North Haven, CT (US)

( * ) Notice: Subject to any disclaimer, the term of this patent is extended or adjusted under 35 U.S.C. 154(b) by 646 days.

This patent is subject to a terminal disclaimer.

(21) Appl. No.: 10/328,494

(22) Filed: Dec. 23, 2002

(65) Prior Publication Data

US 2003/0135229 A1    Jul. 17, 2003

Related U.S. Application Data

(63) Continuation of application No. 08/373,831, filed on Jan. 24, 1995, now Pat. No. 6,497,716, which is a continuation of application No. 08/352,274, filed on Dec. 7, 1994, now Pat. No. 5,486,190, which is a continuation of application No. 08/176,001, filed on Dec. 30, 1993, now abandoned, which is a continuation of application No. 07/693,582, filed on Apr. 30, 1991, now Pat. No. 5,295,993, said application No. 08/352,274 is a continuation-in-part of application No. 08/122,612, filed on Sep. 15, 1993, now Pat. No. 6,197,041, which is a continuation of application No. 07/721,173, filed on Jun. 26, 1991, now abandoned.

(51) Int. Cl.
*A61B 17/34* (2006.01)

(52) U.S. Cl. .................................................... 606/185
(58) Field of Classification Search ............... 606/185; 604/164.01, 156, 158
See application file for complete search history.

(56) References Cited

U.S. PATENT DOCUMENTS

| 1,213,001 A | 1/1917 | Philips |
| 2,496,111 A | 1/1950 | Turkel |
| 2,623,521 A | 12/1952 | Shaw |
| 3,030,959 A | 4/1962 | Grunert |
| 3,605,744 A | 9/1971 | Dwyer |
| 3,643,649 A | 2/1972 | Amato |
| 3,657,812 A | 4/1972 | Lee |
| 3,817,251 A | 6/1974 | Hasson |

(Continued)

FOREIGN PATENT DOCUMENTS

DE    836392    4/1952

(Continued)

*Primary Examiner*—Michael Thaler

(57) ABSTRACT

A safety trocar is provided in which the cannula is reciprocally mounted to the cannula housing and reciprocates into the cannula housing when a proximally directed force is applied thereto. The piercing tip is maintained in the exposed position by a latching mechanism associated with the obturator shaft, and is automatically withdrawn into the cannula under the force of a spring when the proximal force is removed from the cannula, the cannula thus advancing distally and releasing the latching mechanism. Penetration force is maintained at a minimum, and safe and efficacious trocar entry is facilitated.

20 Claims, 9 Drawing Sheets

U.S. PATENT DOCUMENTS

| | | | |
|---|---|---|---|
| 3,882,849 A | 5/1975 | Jamshidi |
| 4,018,228 A | 4/1977 | Goosen |
| 4,168,699 A | 9/1979 | Hauser |
| 4,177,814 A | 12/1979 | Knepshield et al. |
| 4,207,887 A | 6/1980 | Hiltebrandt et al. |
| 4,210,146 A | 7/1980 | Banko |
| 4,220,155 A | 9/1980 | Kimberling et al. |
| 4,254,762 A | 3/1981 | Yoon |
| 4,256,119 A | 3/1981 | Gauthier |
| 4,299,230 A | 11/1981 | Kubota |
| 4,356,826 A | 11/1982 | Kubota |
| 4,375,815 A | 3/1983 | Burns |
| 4,393,587 A | 7/1983 | Kloosterman |
| 4,411,653 A | 10/1983 | Razi |
| 4,414,974 A | 11/1983 | Dotson et al. |
| 4,499,898 A | 2/1985 | Knepshield et al. |
| 4,535,773 A | 8/1985 | Yoon |
| 4,556,059 A | 12/1985 | Adamson, Jr. |
| 4,559,041 A | 12/1985 | Razi |
| 4,601,710 A | 7/1986 | Moll |
| 4,637,393 A | 1/1987 | Ray |
| 4,653,475 A | 3/1987 | Seike et al. |
| 4,654,030 A | 3/1987 | Moll et al. |
| 4,723,545 A | 2/1988 | Nixon et al. |
| 4,730,613 A | 3/1988 | Gordy |
| 4,733,662 A | 3/1988 | Desatnick et al. |
| 4,747,831 A | 5/1988 | Kulli |
| 4,813,940 A | 3/1989 | Parry |
| 4,817,631 A | 4/1989 | Schnepp-Pesch et al. |
| 4,850,973 A | 7/1989 | Jordan et al. |
| 4,869,717 A | 9/1989 | Adair |
| 4,874,375 A | 10/1989 | Ellison |
| 4,902,280 A | 2/1990 | Lander |
| 4,919,653 A | 4/1990 | Martinez et al. |
| 4,931,042 A | 6/1990 | Holmes et al. |
| 4,940,458 A | 7/1990 | Cohn |
| 4,943,280 A | 7/1990 | Lander |
| 4,955,870 A | 9/1990 | Ridderheim et al. |
| 4,986,814 A | 1/1991 | Burney et al. |
| 5,009,643 A | 4/1991 | Reich et al. |
| 5,013,294 A | 5/1991 | Baier |
| 5,030,206 A | 7/1991 | Lander |
| 5,066,288 A | 11/1991 | Deniega et al. |
| 5,073,169 A | 12/1991 | Raiken |
| 5,104,382 A | 4/1992 | Brinkerhoff et al. |
| 5,104,383 A | 4/1992 | Schichman |
| 5,116,353 A | 5/1992 | Green |
| 5,127,909 A | 7/1992 | Schichman |
| 5,152,754 A | 10/1992 | Plyley et al. |
| 5,158,552 A | 10/1992 | Borgia et al. |
| 5,226,426 A | 7/1993 | Yoon |
| 5,267,965 A | 12/1993 | Deniega |
| 5,290,243 A | 3/1994 | Chodorow |
| 5,290,304 A | 3/1994 | Storace |
| 5,318,580 A | 6/1994 | Gresl, Jr. |
| 5,320,610 A | 6/1994 | Yoon |
| 5,324,268 A | 6/1994 | Yoon |

FOREIGN PATENT DOCUMENTS

| | | |
|---|---|---|
| EP | 350291 | 1/1990 |
| EP | 479130 | 9/1991 |
| EP | 0479130 | 4/1992 |
| SU | 344853 | 4/1972 |
| SU | 537677 | 1/1977 |
| SU | 921554 | 4/1982 |
| WO | WO89 03661 | 5/1989 |
| WO | WO93 04632 | 3/1993 |
| WO | WO93 04715 | 3/1993 |
| WO | WO93 04716 | 3/1993 |

FIG. 3
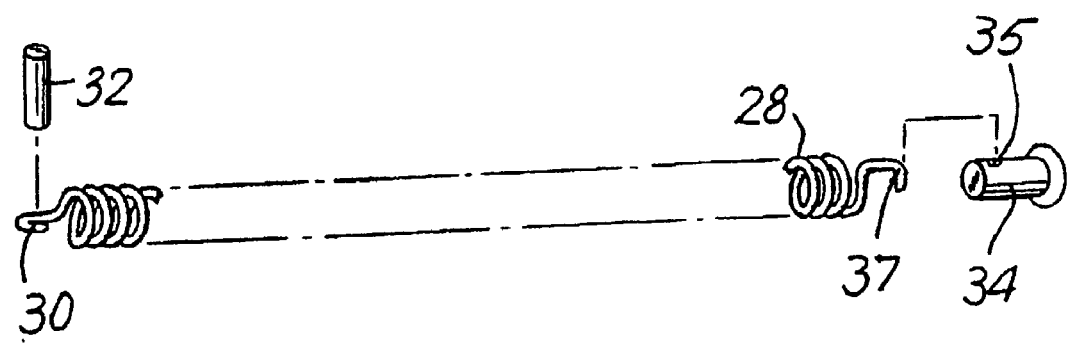
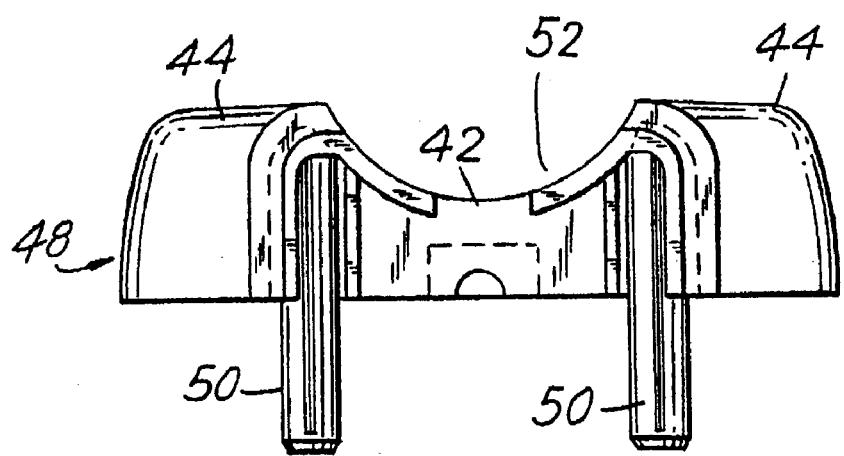
FIG. 4

SAFETY TROCAR

CROSS-REFERENCE TO RELATED APPLICATIONS

This application is a continuation of application Ser. No. 08/373,381, filed Jan. 24, 1995, now U.S. Pat. No. 6,497,716, which is a continuation of application Ser. No. 08/352,274, filed Dec. 7, 1994, now U.S. Pat. No. 5,486,190, which is a continuation of application Ser. No. 08/176,001, filed Dec. 30, 1993, now abandoned, which is a continuation of application Ser. No. 07/693,582, filed Apr. 30, 1991, now U.S. Pat. No. 5,295,993. The '274 application is also a continuation-in-part of application Ser. No. 08/122,612, filed Sep. 15, 1993, now U.S. Pat. No. 6,197,041, which is a continuation of application Ser. No. 07/721,173, filed Jun. 26, 1991, now abandoned.

BACKGROUND

1. Technical Field

This invention relates to a surgical trocar and more particularly to a safety trocar in which the sharp cutting tip retracts into the cannula so as to minimize the likelihood of inadvertent injury to viscera and other internal tissue.

2. Background of Related Art

Trocars are sharp pointed surgical instruments used to puncture a body cavity. Trocars are generally adapted to be used together with a tubular trocar sleeve or cannula. Once the body cavity has been punctured by the trocar, the sharp trocar is removed from the cannula, thereby leaving the cannula extending into the body cavity. Endoscopic surgical procedures are then performed through the cannula with accessory instrumentation such as laparoscopes, dissectors, graspers, etc.

Commercially available safety trocars include a spring-loaded safety shield which is adapted to cover the trocars tip once the body cavity has been entered so as to provide an increased level of protection to internal structures from puncture of laceration. For example, U.S. Pat. No. 4,601,710 to Moll describes a trocar assembly which consists of two subassemblies: a trocar subassembly which includes a sharp-tipped trocar and a spring-loaded tubular safety shield positioned therearound, and a cannula subassembly.

When ready for use, the trocar and safety shield of the trocar subassembly are inserted through the cannula. The safety shield is initially in its distal-most position covering the trocar tip. Exertion of pressure against the skin with the trocar causes the shield to be pushed rearwardly against the spring to expose the piercing tip of the trocar. The tip penetrates the skin and underlying tissue with continued pressure. Once the tip has penetrated through the wall and has entered the cavity, the force against the front end of the shield ceases and the shield is automatically moved back to its distally extended position. Viscera and other internal tissue are thus protected from contact with the sharp piercing tip and potential damage therefrom.

An article entitled "Needle for the Puncture and Lavage of the Abdominal Cavity" authored by F. S. Subairov discloses a safety device for puncturing the abdominal cavity which consists of a hollow tube, a stylet and a spring. The spring is soldered to the stylet and threaded into the rear of the hollow tube. The distal end of the stylet is exposed from the hollow tube by pressing the stylet toward the tube, thereby compressing the spring. Once the stylet and tube enter a body cavity, the tube is advanced under spring force to cover the distal end of the stylet. A similar device is disclosed in EP 350,291 (see FIGS. 1–4).

U.S. Pat. No. 4,535,773 to Yoon suggests several alternative safety trocar designs. In one embodiment (see FIGS. 22–28), a spring-loaded blunt probe is provided within the trocar shaft, as with conventional Verres needles. The blunt probe is adapted to reciprocally slide through an aperture in the trocar tip such that when the trocar tip enters a body cavity, the blunt probe springs distally forward through the aperture to prevent contact between the trocar tip and body organs. In a second embodiment (see FIGS. 33–36), pressure sensors or transducers are fitted into the trocar blade surfaces and the distal end of the cannula. Sets of electrical leads run through the trocar shaft and communicate with an alarm network in the proximal portion of the device. A further modification is suggested in which the trocar shaft is initially manually extended and maintained in its extended position by a detent which protrudes through a hole in the surrounding tubular structure. The hole aligns with a solenoid socket. When the instrument is fully assembled and the trocar tip is forced through a body wall, the electrical leads running through the trocar shaft send electrical signals to the solenoid which, at the appropriate instant, forces the detent from the hole, allowing the trocar tip to withdraw into the cannula. Additional mechanisms for effecting withdrawal of cutting implements are also known. See, e.g., U.S. Pat. No. 4,375,815 to Burns; U.S. Pat. No. 3,657,812 to Lee; and U.S. Pat. No. 3,030,959 to Grunert.

SUMMARY

It has now been found that an improved safety trocar may be provided which includes:

(a) a cannula assembly comprising a cannula and a cannula housing;

(b) a trocar assembly comprising a sharp trocar tip, an obturator shaft, and a trocar housing;

(c) means associated with the obturator shaft which releasably maintains the trocar tip in an extended position;

(d) means associated with the cannula assembly for releasing the releasable obturator means; and (e) biasing means for retracting the trocar tip from the extended position to a retracted position in response to release of the releasable obturator means.

The safety trocar of the present invention is adapted to be armed by the surgeon immediately prior to use. Arming may be accomplished by advancing a button which extends through the trocar housing, by compressing the trocar housing toward the cannula housing, or by like means. Once armed, the trocar tip releasably protrudes beyond the distal end of the cannula.

As the surgeon presses the trocar, and more particularly the trocar tip, against the body wall of a patient, an incision into and through the body wall is begun. With continued pressure by the surgeon, the distal end of the cannula comes into contact with the body wall. The initial counterforce exerted by the body wall against the cannula causes a mechanism associated with the cannula to position the obturator shaft (together with the cutting tip) for immediate retraction upon entry of distal end of the cannula into the body cavity. Thus, removal of the counterforce from the distal end of the cannula, e.g., upon entering the body cavity, results in immediate and automatic withdrawal of the trocar tip into the cannula under the force of a biasing means, e.g., a spring.

In a preferred embodiment of the trocar, a latch is associated with the obturator shaft to which the trocar tip is mounted, the latch being biased radially outward and being adapted to engage an internal shelf formed in the cannula when the trocar is armed. The cannula is reciprocally mounted to the cannula housing and biased, e.g., by a compression spring, distally relative to the cannula housing. As the trocar tip enters the body cavity and the body wall exerts force on the distal end of the cannula, the cannula reciprocates proximally into the cannula housing. This cannula reciprocation repositions the cannula's internal shelf relative to the latch such that, upon distal movement of the cannula upon entry into the body cavity, the latch is released from engagement with the internal shelf. A spring which was loaded upon arming the trocar is thus free to immediately retract the trocar tip into the cannula. In a particularly preferred trocar embodiment, abutment means are provided on the exterior of the cannula toward its distal end to facilitate reciprocation thereof through contact with the body wall.

The trocar of the invention is also designed to permit manual retraction or disarming of the cutting tip, if so desired. This is accomplished by manually reciprocating the cannula housing and releasing, thereby disengaging the latch from the internal shelf. The trocar is also typically provided with an indicator which signals the surgeon as to whether the trocar is armed or disarmed. For example, the relative position of the button used to arm the trocar may be calibrated or indexed to communicate the trocar tip position or a window may be provided through which a trocar tip position indicator is visible.

The trocar of the present invention provides a safe and efficacious means for gaining access to body cavities to permit minimally-invasive diagnostic and surgical procedures to be accomplished. The trocar is equipped with a reliable mechanism for effectuating immediate, automatic retraction of the cutting tip into the cannula. Penetration force is kept to a minimum through the unique internal mechanism for releasably maintaining the trocar tip in the armed position.

BRIEF DESCRIPTION OF THE DRAWINGS

The present invention will become apparent from the following detailed description taken in conjunction with the accompanying drawings in which:

FIG. 3 is an exploded view of a spring assembly;

FIG. 4 is a front view of a top trocar housing;

BRIEF DESCRIPTION OF PREFERRED EMBODIMENTS

Figure 1:
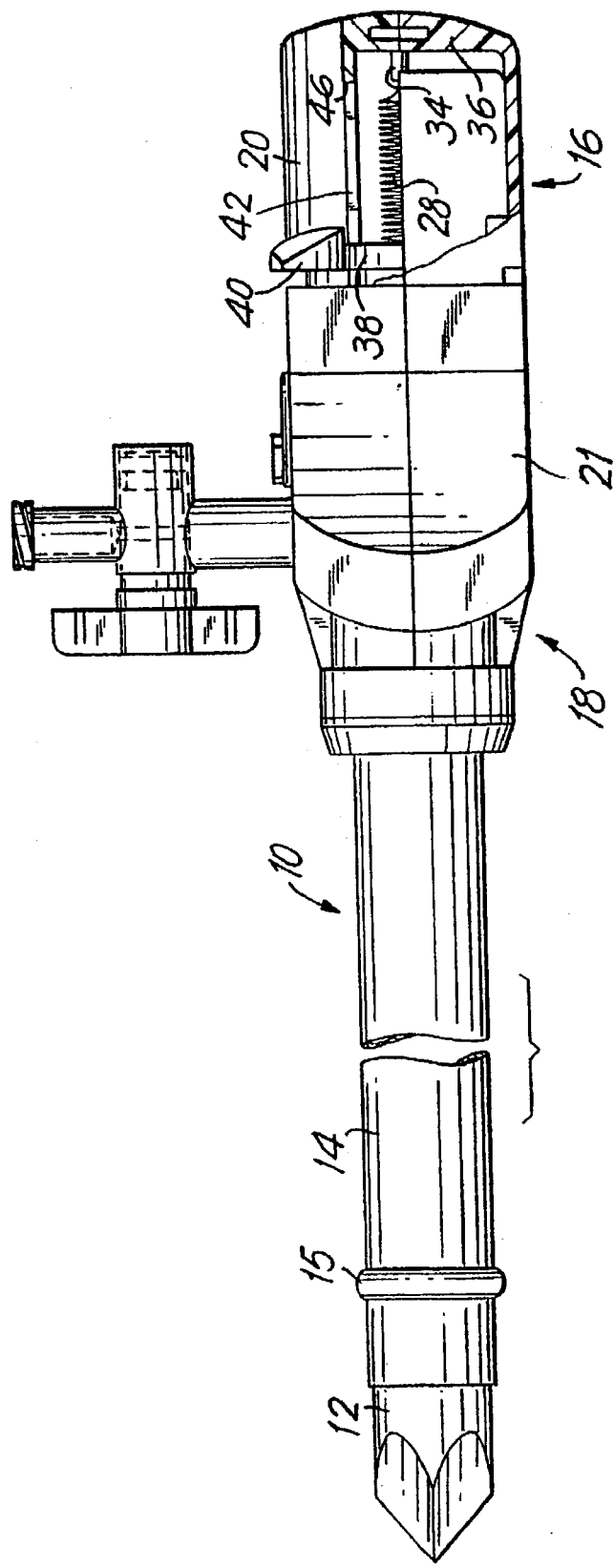
FIG. 1 is a side view of a trocar of the present invention in an armed configuration.

Referring to FIG. 1, trocar 10 is shown in its fully assembled condition with cutting tip 12 extending from cannula 14. Trocar 10 includes a trocar assembly 16 and a cannula assembly 18. The longitudinally extending or endoscopic portion of trocar assembly 16 which extends from trocar housing 20 is shielded from view in FIG. 1 by cannula housing 21 and cannula 14, except for extended cutting tip 12. A circumferential abutment surface 15 is provided toward the distal end of cannula 14.

Figure 2:
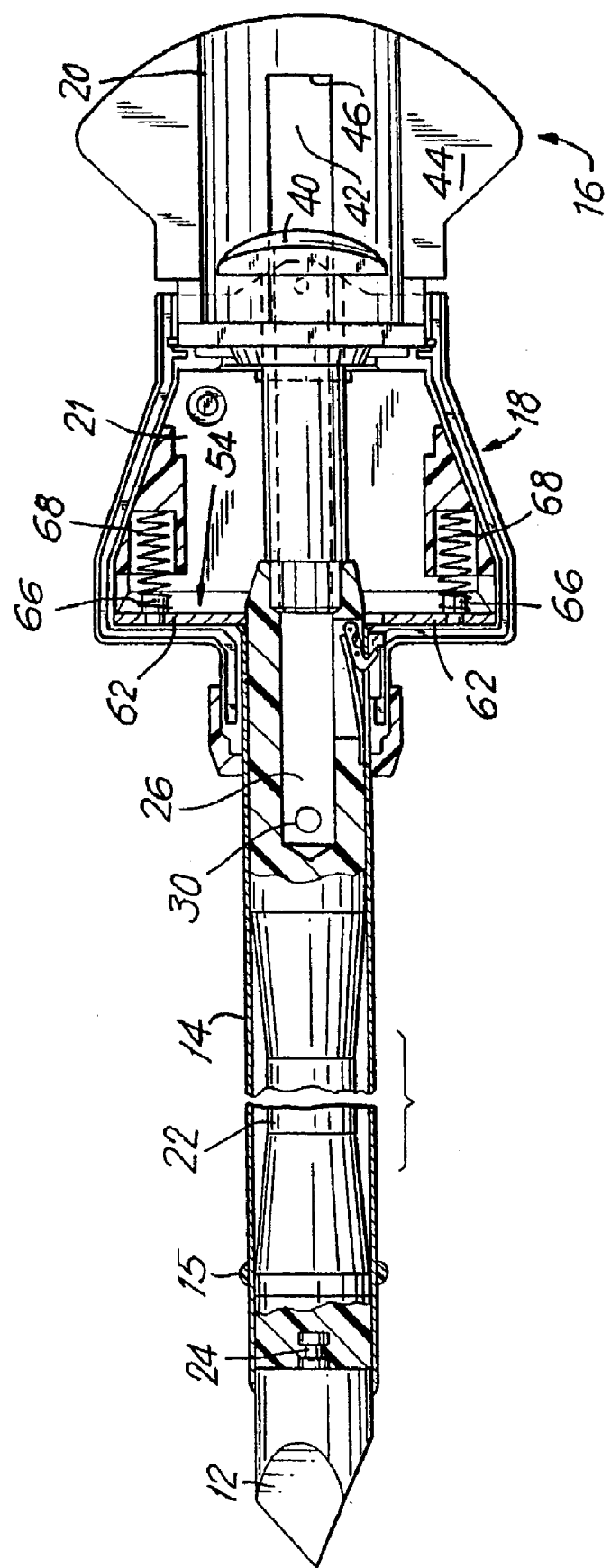
FIG. 2 is a top view of the trocar assembly of FIG. 1, partially in cross section.
Figure 5:
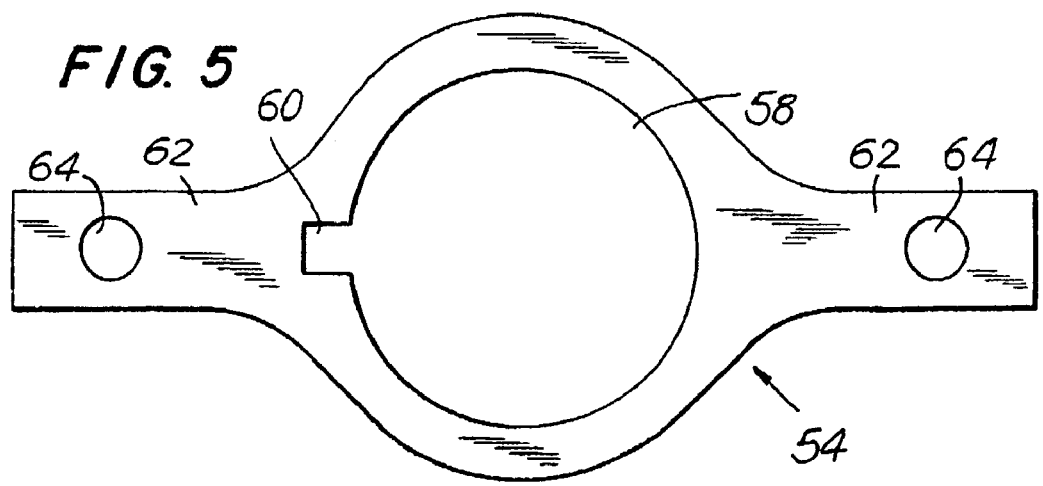
FIGS. 5 and 6 are plan and side views, respectively, of a spring-retaining plate.
Figure 6:
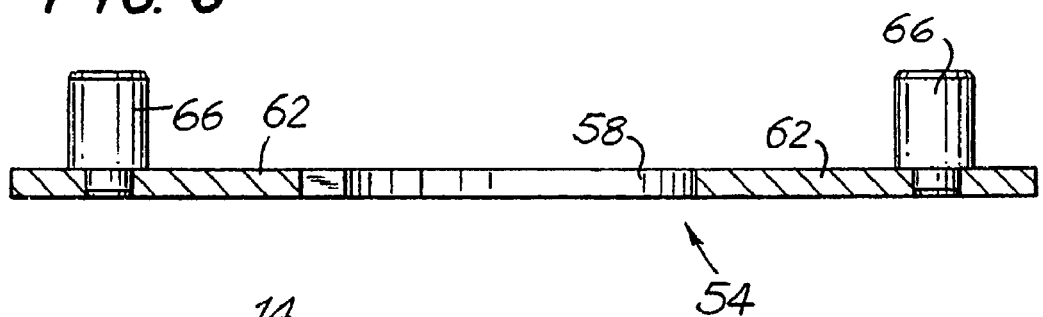
Figure 7:
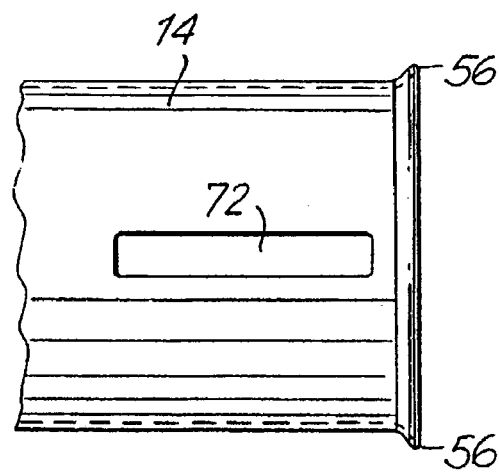
FIGS. 7 and 8 are partial side views of the cannula.
Figure 8:
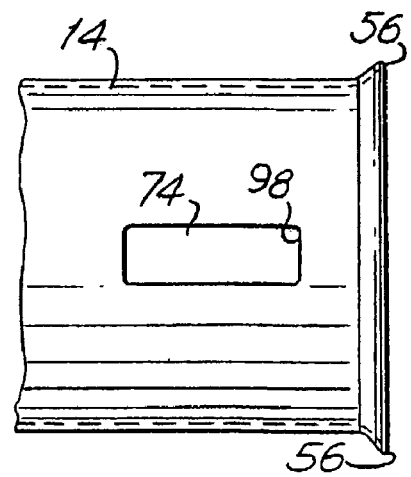

Referring now to FIGS. 2 and 3, pyramidal cutting tip 12 is rotatably mounted to obturator shaft 22 at swivel joint 24. A cylindrical channel 26 is formed in the proximal end of obturator shaft 22. A tension spring 28 (see FIGS. 1 and 3) is positioned within channel 26 and anchored to obturator shaft 22 at distal extension 30 by pin 32. An anchor pin 34 which is adapted to mount to rear wall 36 of trocar housing 20 includes an aperture 35 which cooperates with proximal arm 37 to anchor tension spring 28 to trocar housing 20.

A flange 38 is formed at the proximal end of obturator shaft 22 encircling tension spring 28. Flange 38 forms a half-moon shaped button 40 which slides within slot 42 in the upper face 44 of trocar housing 20. Movement of button 40 within slot 42 moves obturator shaft 22 and cutting tip 12 relative to trocar housing 20. Tension spring 28 biases obturator shaft 22 and its accompanying structure proximally, such that flange 38 rests against rear face 46 of slot 42 absent external influences.

Figure 11:
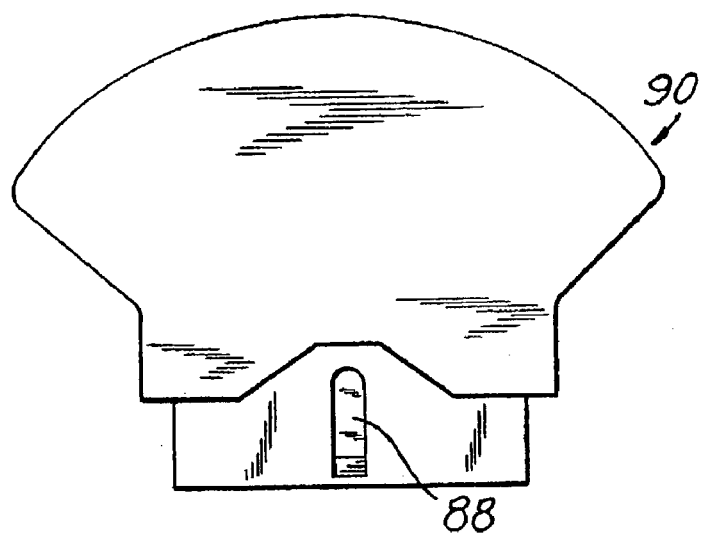
FIG. 11 is a bottom view of a trocar housing.

Referring to FIG. 4, top housing 48 of trocar housing 20 is shown. Top housing 48 includes mounting legs 50 for attachment to a bottom housing 90 (FIG. 11). Upper face 44 includes a concave region 52 in the base of which is formed slot 42. As most clearly seen in FIG. 1, button 40 is sized and dimensioned to conform to and slide within concave region 52 while extending slightly above upper face 44 of trocar housing 20. The cooperation between concave region 52 and button 40 facilitates unimpeded movement of button 40, particularly upon retraction of trocar tip 12 as discussed below, without sacrificing convenient thumb access to button 40 for arming of trocar 10 by the surgeon.

Turning to cannula assembly 18, cannula 14 defines a tubular lumen and is reciprocally mounted to cannula housing 21. Referring to FIGS. 2 and 5–8, a spring-retaining plate 54 is mounted to flange 56 at the proximal end of cannula 14, e.g., by adhesive or welding, with central aperture 58 in plate 54 aligned with the lumen through cannula 14. Aperture 58 is sized to accommodate unencumbered passage of obturator shaft 22 and includes oppositely directed extension arms 62, each arm 62 having an aperture 64. Apertures 64 receive and frictionally engage cylindrical pins 66. Aperture extension 60 is formed in one extension arm 62 allowing passage of latch subassembly 147 therethrough, as described below.

Referring again to FIG. 2, cannula housing 21 receives spring-retaining plate 54 with cylindrical pins 66 facing proximally. Compression springs 68 are positioned against extension arms 62 and around pins 66. Pins 66 thus act to position and support springs 68. Chambers 70 are formed in cannula housing 21 to receive and capture the opposite ends of compression springs 68. Reciprocation of cannula 14 into cannula housing 21 causes proximal movement of plate 54 which compresses springs 68 within chambers 70, thereby biasing cannula 14 in the distal direction.

Figure 9:
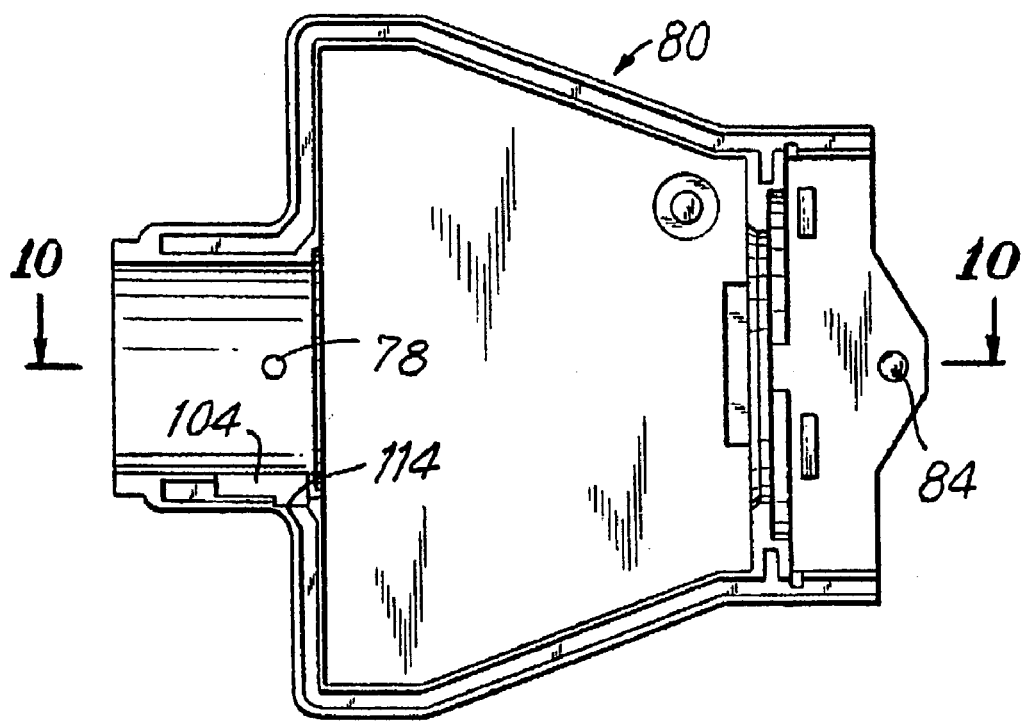
FIG. 9 is a plan view of a lower cannula housing.
Figure 10:
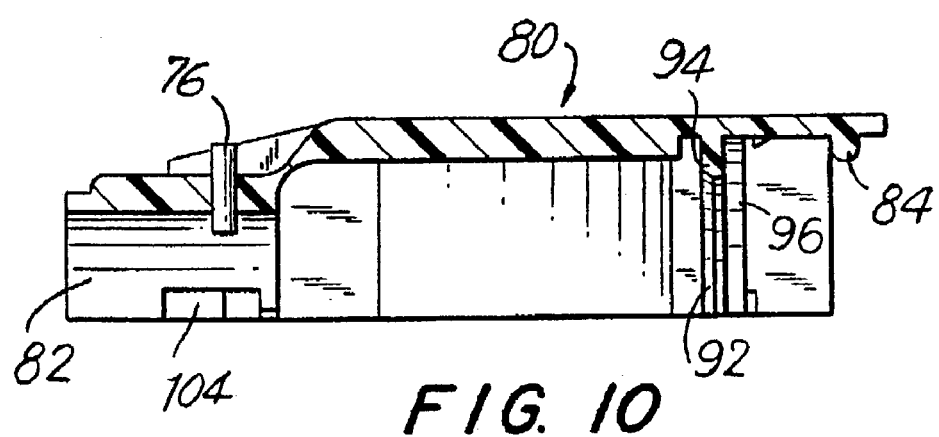
FIG. 10 is a sectional side view of the cannula housing of FIG. 9 taken along line 10—10.

Returning to FIGS. 7 and 8, the proximal end of cannula 14 includes two slots 72 and 74, preferably separated by at least 90.degree. Alignment slot 72 serves to maintain rotational alignment of cannula 14 with respect to cannula housing 21. Referring additionally to FIGS. 9 and 10, alignment pin 76 is fixedly secured within aperture 78 in lower cannula housing 80 and, when fully inserted into housing 80, extends into lumen 82. In assembling cannula 14 within lower cannula housing 80, alignment pin 76 is positioned within alignment slot 72, thereby preventing rotation of cannula 14 yet permitting axial movement of cannula 14 relative to cannula housing 21. Additionally, inwardly directed orientation pin 84 on proximal housing extension face 86 cooperates with an orientation slot 88 in bottom housing 90 (see FIG. 11) to ensure proper alignment between cannula housing 21 and trocar housing 20. A gasket 92 and stabilizer plate 96 are positioned within flange 94 in lower cannula housing 80 to provide a gas seal with inserted instrumentation, and to cooperate with an internal flapper valve, as is known in the art.

Figure 12:
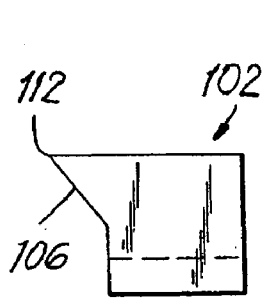
FIG. 12 is a side view of a shelf insert.
Figure 13:
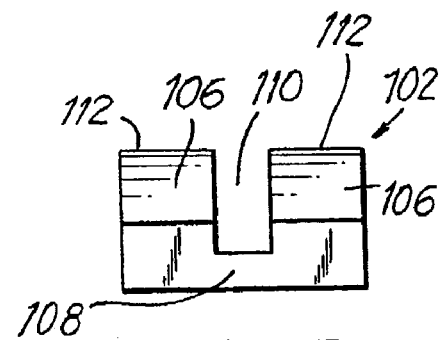
FIG. 13 is a front view of the shelf insert of FIG. 12.
Figure 14:
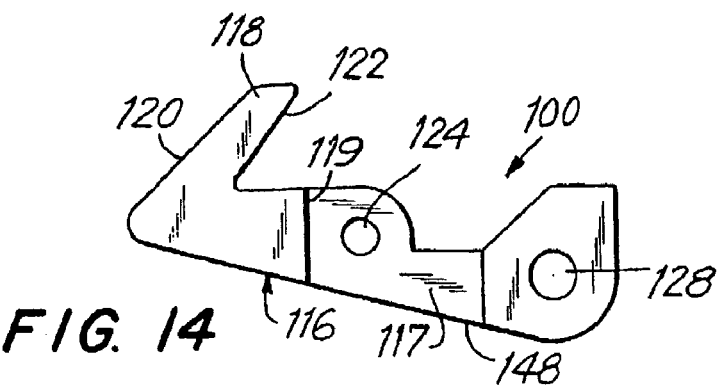
FIG. 14 is a side view of a latch.

Slot 74 in cannula 14 forms an internal shelf 98 with which latch 100 (see FIG. 14) is adapted to engage. Internal shelf insert 102 (FIGS. 12 and 13) is positional within cavity 104 in lower cannula housing. Shelf insert 102 comprises angled latching faces 106, bridging arm 108 and longitudinal slot 110. Shelf insert 102 is positioned within cavity 104 such that angled latching faces 106 are directed distally and edges 112 are substantially aligned with internal shelf 98 of cannula 14. Bridging arm 108 abuts outer wall 114 of cavity 104 and is typically secured thereto, e.g., by an adhesive.

Figure 15:
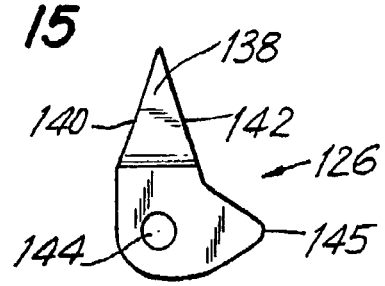
FIG. 15 is a side view of a latch release finger.
Figure 17:
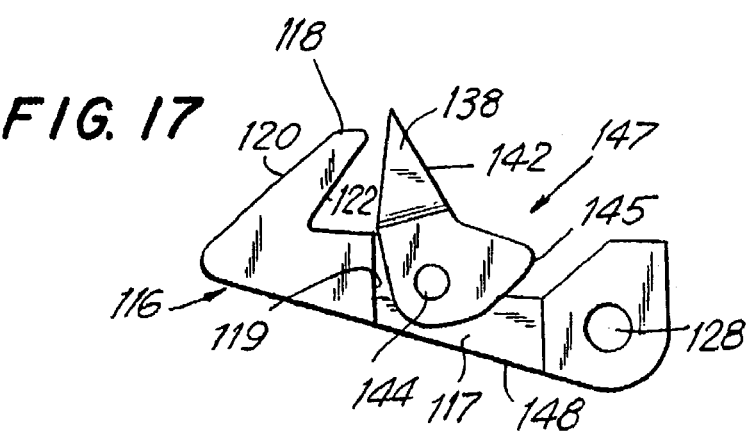
FIG. 17 is a side view of a latch subassembly.
Figure 18:
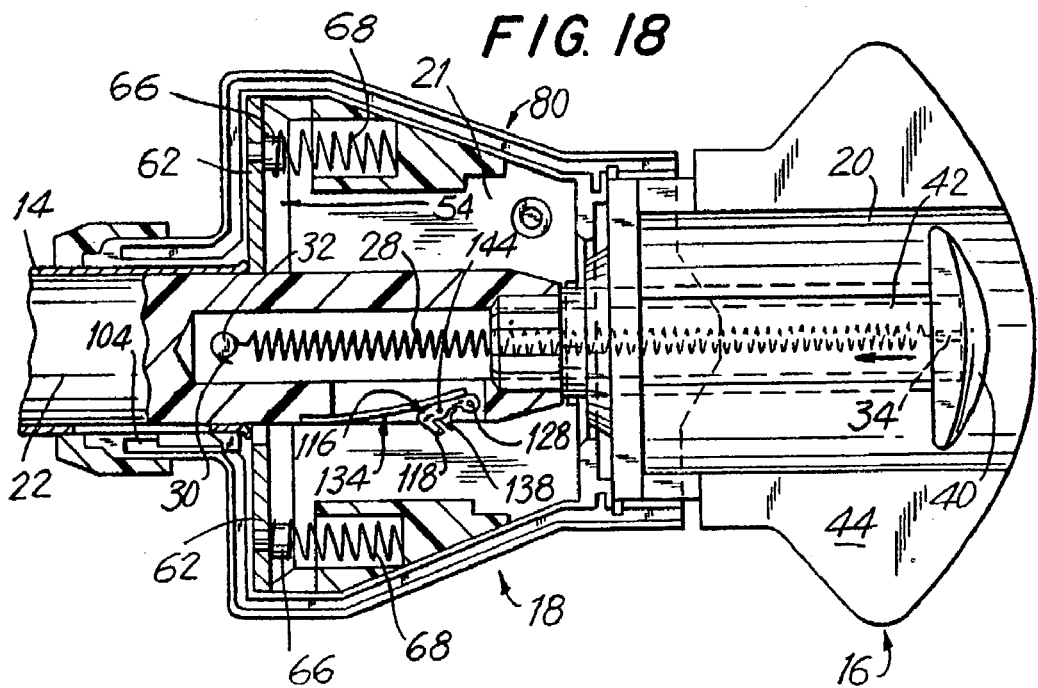
FIG. 18 is a top view, partially in section, of the proximal end of an unarmed trocar of the present invention.
Figure 19:
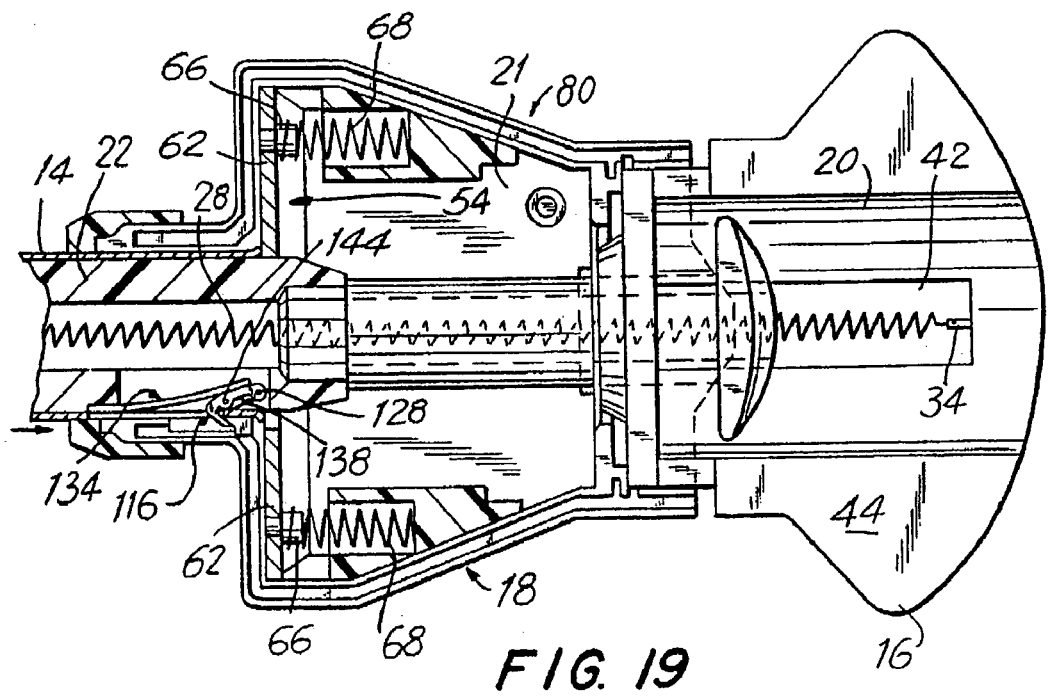
FIGS. 19–21 are top views, partially in section, of the proximal end of an armed trocar of the present invention showing a sequence of positions which culminate in retraction of the trocar tip.
Figure 20:
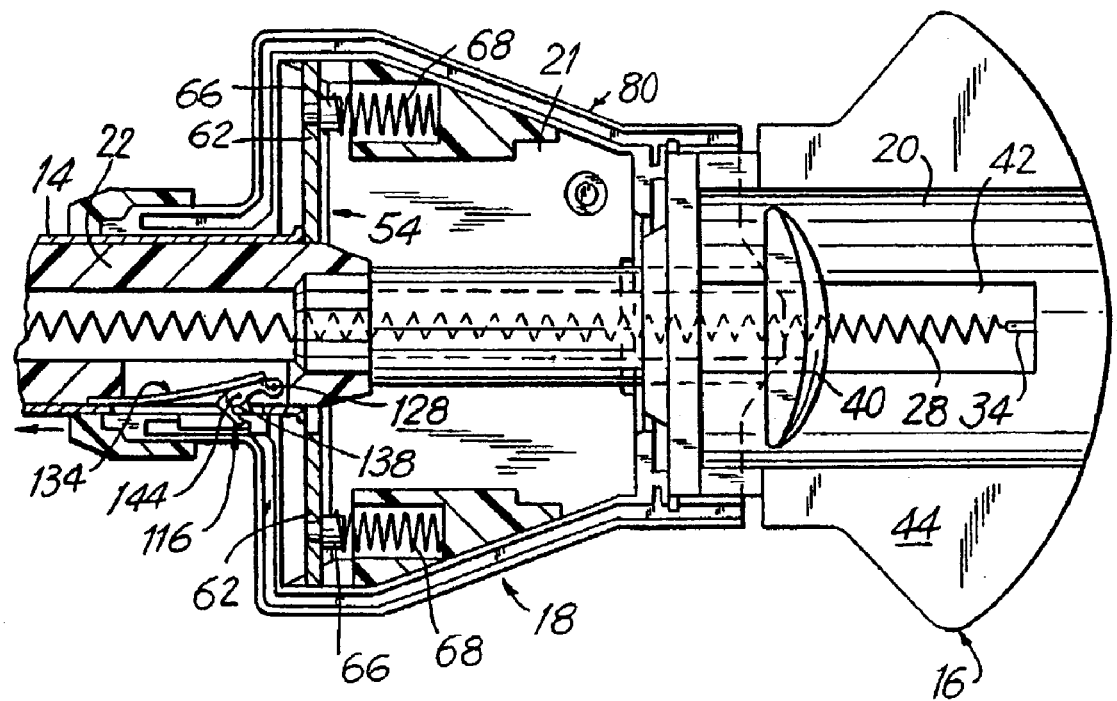
Figure 21:
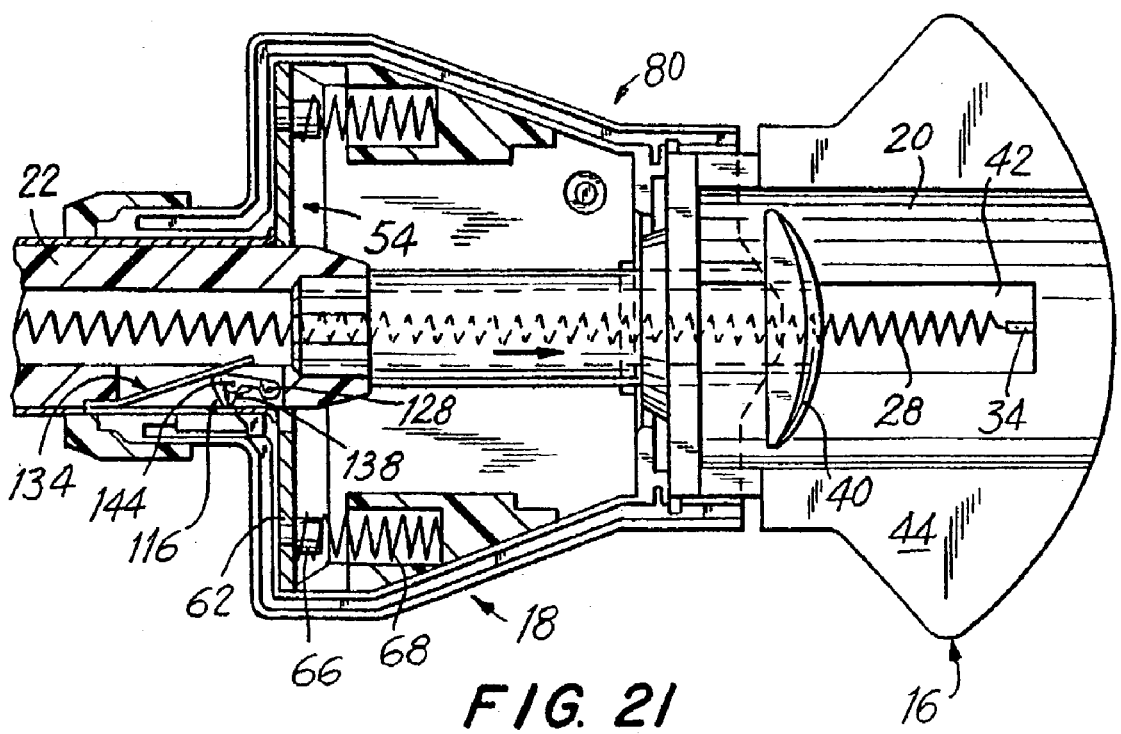

Latch 100 has a body 116 which forms a latch finger 118 which includes an outer camming face 120 and an inner latching face 122. Aperture 124 is located in mid-region 117 of body 116 and permits latch 100 to be movably joined to latch release finger 126 (see FIGS. 15 and 17). Mid-region 117 is of reduced thickness relative to the remainder of body 116 to accommodate latch release finger 126. Aperture 128 is formed in the region of body 116 distant from latch finger 118.

Figure 16:
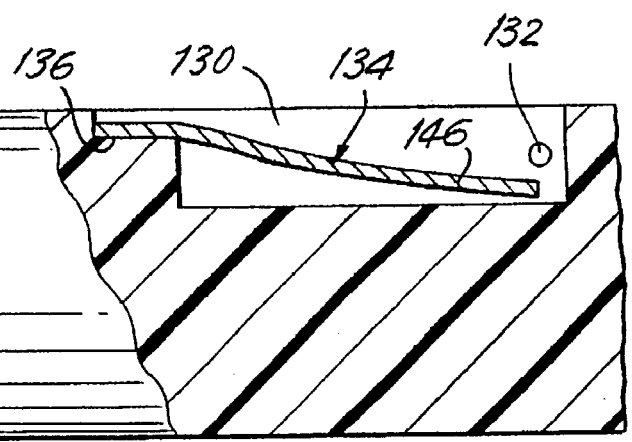
FIG. 16 is a side view, partially in section, of a portion of a cannula.

Latch release finger 126 includes a substantially triangularly-shaped extension 138 having distal and proximal cam faces 140 and 142, respectively. Latch release finger 126 also includes an aperture 144 and a spring abutment region 145. As shown in FIG. 16, latch release finger 126 is movably mounted to latch 100 by means of a pin (not pictured) which passes through apertures 144 and 124 to form a latch subassembly 147. When release finger 126 is positioned such that extension 138 is directed toward aperture 128, abutment region 145 extends below latch wall 148.

Latch subassembly 147 is pivotally joined to obturator shaft 22 by a pin (not pictured) which passes through aperture 128 in latch body 116 and aperture 132 in hollow region 130 of shaft 22. As shown in FIG. 16, a leaf spring 134 is mounted to shelf 136 in hollow region 130, e.g., by an adhesive. The proximal region 146 of leaf spring 134 biases latch 100 clockwise around aperture 128 and biases release finger 126 counter-clockwise relative to aperture 144. Hollow region 130 is sized and dimensioned to permit latch subassembly 147 to be fully recessed therewithin (against the bias of leaf spring 134). Inasmuch as release finger 126 is restricted in its counter-clockwise rotation by latch finger 118 and/or abutment with wall 119, and in its clockwise rotation by engagement between spring abutment region 145 and leaf spring 134, the full range of rotation of release finger 126 is approximately 90.degree.

In use, and referring generally to FIGS. 18–21 cutting tip 12 and obturator shaft 22 are introduced through cannula housing 21 and into cannula 14. When obturator shaft 22 is fully inserted, trocar housing 16 abuts cannula housing 21. However, cutting tip 21 remains within cannula 14 until trocar 10 is armed by the surgeon. To arm the instrument, the surgeon advances button 40 within channel 42 which distally advances obturator shaft 22 and causes cutting tip 12 to extend beyond cannula 14. Distal movement of obturator shaft 22 also results in distal movement of latch subassembly 147.

Leaf spring 134 biases latch subassembly 147 outward from hollow region 130. As obturator shaft 22 moves distally, outwardly biased latch subassembly 147 passes through aperture extension 60 in spring-retaining plate 54. Outer camming face 120 of latch 100 then contacts flange 56 at the proximal end of cannula 14, causing counterclockwise rotation of latch subassembly 147 relative to aperture 128 (see FIG. 17). This counterclockwise rotation recesses latch subassembly 147 within hollow region 130 against the bias of leaf spring 134.

As cutting tip 12 approaches its fully armed position, latch subassembly 147 comes into alignment with slot 74 in cannula 14. Outer camming face 120 is thus freed from contact with the inner surface of cannula 14, and leaf spring 134 causes latch subassembly 147 to rotate clockwise such that latch finger 118 extends radially outward from hollow region 130. However, latch release finger 126 remains positioned such that extension 138 is directed substantially toward aperture 128, with abutment region 145 resting against leaf spring 134. The freeing of camming face 120 from contact with cannula 14 is generally accompanied by an audible click, signalling the surgeon that trocar 10 is armed and further distal movement of button 40 is unnecessary.

When the surgeon releases button 40, tension spring 38 draws obturator shaft 22 proximally until inner latching face 122 of latch 100 engages internal shelf 98 and shelf insert 102. Latch release finger 126 passes back within cannula 14 proximal of slot 74, thereby pressing abutment region 145 against the bias of leaf spring 134. In this fully armed position of FIGS. 1 and 2, cutting tip 12 extends beyond cannula 14 and button 40 is distally located within slot 42.

The surgeon presses armed trocar 10 against the body wall of a patient, thus causing piercing tip 12 to incise the tissue. As cutting tip 12 passes through the body wall, the distal end of cannula 14 is brought into engagement with tissue. The counterforce exerted by the body wall against cannula 14 and abutment surface 15 causes cannula 14 to move proximally against the bias of compression springs 68. This proximal movement of cannula 14 release latch release finger 126 to enter slot 74. Latch release finger 126 rotates counterclockwise relative to aperture 144 within longitudinal slot 110 in shelf insert 102.

As the surgeon continues to press trocar 10 against the body wall, piercing tip 12 enters the body cavity. Continued pressure by the surgeon advances cannula 14 into the body cavity as well. As soon as the counterforce of the body wall against the distal end of the cannula 14 and abutment surface 15 is surpassed by the distally-directed force of compression springs 68 against spring-retaining plate 54, cannula 14 is driven distally relative to cannula housing 18. As cannula 14 moves distally, internal shelf 98 contacts proximal cam face 142 of latch release finger 126. Latch release finger 126 is thus driven counterclockwise such that extension 138 abuts latch finger 118 and/or the body of latch release finger 126 abuts wall 119 of latch 100. In this position, latch release finger 126 prevents engagement between internal shelf 98 and latch finger 118.

As cannula 14 continues to move distally, internal shelf 98 cams latch subassembly 147 counterclockwise relative to aperture 128 against the bias of leaf spring 134, thus freeing latch finger 118 from engagement with shelf insert 102. As soon as the tip of latch finger 118 rotates out of engagement with shelf insert 102, tension spring 28 draws obturator shaft 22 and cutting tip 12 proximally such that cutting tip 12 is positioned within cannula 14. Button 40 is also drawn proximally within slot 42 and is once again positioned to allow the surgeon to arm trocar 10, if so desired.

If, after arming trocar 10, the surgeon determines that it is desirable to manually retract cutting tip 12 into cannula 14, the surgeon simply moves cannula 14 proximally with respect to cannula housing 18 and releases. Cannula 14 will then move distally under the bias of compression springs 68 rotating latch subassembly 147 counterclockwise. Latch finger 118 is thus moved out of engagement with shelf insert 102, allowing tension spring 28 to withdraw cutting tip 12 into cannula 14.

The position of button 40 within slot 42 provides the surgeon with a visual indication of the position of cutting tip 12 relative to cannula 14. The audible click associated with the movement of latch 100 during the arming of trocar 10 also provides an aural signal to the surgeon.

Many structures may be included toward the distal end of cannula 14 to facilitate the sensing of body wall counterforce to effectuate reciprocation of cannula 14, abutment surface 15 being but one example. Exemplary structures include radially spaced, outwardly directed protuberances, inflatable means of the type known in the art for fixedly positioning catheters and like devices, and flange means of varying geometries. Such structures may be fixedly secured to cannula 14 or repositionable along the longitudinal axis of cannula based on such factors as patient size and weight.

While the above description contains many specific details, these details should not be construed as limitations on the scope of the invention, but merely as examples of preferred embodiments thereof. Those skilled in the art will envision many other possible variations that are within the scope and spirit of the invention as defined by the claims appended hereto.

What is claimed is:

1. An apparatus for penetrating tissue, which comprises:
    a housing;
    an elongated member extending distally from the housing, the elongated member having a penetrating end adapted to penetrate tissue, the elongated member adapted for reciprocal longitudinal movement relative to the housing between a retracted position and an extended position; and
    a sleeve member coaxially mounted about the elongated member and adapted for longitudinal movement relative to the housing, the sleeve member operatively associated with the elongated member whereby longitudinal movement of the sleeve member relative to the elongated member and in a distal direction causes corresponding movement of the elongated member from the extended position to the retracted position.

2. The apparatus according to claim 1 including a latch member positioned to releasably secure the elongated member in the extended position.

3. The apparatus according to claim 2 wherein the latch member is operatively associated with the sleeve member whereby movement of the sleeve member causes actuation of the latch member to thereby cause release of the elongated member to permit the elongated member to move to the retracted position thereof.

4. The apparatus according to claim 2 wherein the latch member is adapted to permit movement of the elongated member to the retracted position upon movement of the sleeve member in a general distal direction.

5. The apparatus according to claim 4 wherein the elongated member is normally biased toward the retracted position.

6. The apparatus according to claim 4 wherein the latch member is mounted to one of the elongated member and the housing.

7. The apparatus according to claim 6 wherein the latch member is mounted to the elongated member and is adapted to releasably engage an internal shelf of one of the housing and the sleeve member to releasably secure the elongated member in the extended position thereof.

8. The apparatus according to claim 7 including a spring member operatively connected to the elongated member for normally biasing the elongated member toward the retracted position thereof.

9. The apparatus according to claim 6 wherein the latch member is normally biased to a position to secure the elongated member in the extended position.

10. A trocar for providing access to an underlying body cavity, which comprises:
    a housing;
    a sleeve member mounted to the housing and defining a longitudinal axis, the sleeve member adapted for longitudinal movement relative to the housing; and
    an obturator at least partially disposed within the sleeve member and having a penetrating end adapted to pass through tissue, the obturator adapted for longitudinal movement relative to the housing between a proximal retracted position and a distal advanced position, the obturator movable to the proximal retracted position in response to movement of the sleeve member in a distal direction.

11. The trocar according to claim 10 wherein the sleeve member is adapted for longitudinal movement relative to the obturator between a first position where the penetrating end of the obturator is exposed to penetrate tissue and a second position where the penetrating end is substantially contained within the sleeve member.

12. The trocar according to claim 10 including a latch member mounted to the obturator, the latch member operatively engageable with one of the housing and the sleeve member to releasably secure the obturator in the distal advanced position.

13. The trocar according to claim 12 wherein the latch member is adapted to disengage the one of the trocar housing and the sleeve member during movement of the sleeve member in the distal direction, to thereby permit the obturator to move to the proximal retracted position.

14. The trocar according to claim 13 wherein the obturator is normally biased toward the proximal retracted position.

15. A trocar for providing access to an underlying body cavity, which comprises:
    a cannula assembly including a cannula housing and a cannula sleeve extending from the cannula housing, and defining a longitudinal axis; and
    a trocar assembly at least partially positionable within the cannula assembly, the trocar assembly including a trocar housing for mating with the cannula housing and an obturator extending from the trocar housing, the obturator having a penetrating end for passing through tissue, the obturator being adapted for longitudinal movement relative to the longitudinal axis in a first longitudinal direction in response to longitudinal movement of the cannula sleeve in a second longitudinal direction opposed to the first longitudinal direction.

16. The trocar according to claim 15 including a latch member positioned to operatively releasably secure the obturator in an extended position wherein the penetrating end is at least partially exposed beyond the sleeve to penetrate tissue.

17. The trocar according to claim 16 wherein the latch member is operatively associated with the sleeve member whereby movement of the sleeve member in the second longitudinal direction causes the latch member to operatively release the obturator to permit the obturator to move in the first longitudinal direction to a retracted position thereof wherein the penetrating end is substantially confined within the sleeve.

18. The trocar according to claim 17 wherein the first longitudinal direction is a proximal direction and the second longitudinal direction is a distal direction.

19. The trocar according to claim 18 wherein the first longitudinal direction is a proximal direction and the second longitudinal direction is a distal direction.

20. The trocar according to claim 15 wherein the cannula sleeve is adapted for reciprocal longitudinal movement relative to the cannula housing and wherein the obturator is adapted for reciprocal longitudinal movement relative to the trocar housing.

* * * * *